US012751986B2

(12) United States Patent
Chung et al.

(10) Patent No.: US 12,751,986 B2
(45) Date of Patent: Oct. 6, 2026

(54) **COMPOSITION FOR INHIBITING PROLIFERATION OF TUMOR COMPRISING *RUBUS COREANUS* EXTRACT AS EFFECTIVE COMPONENT**

(71) Applicant: KOREA INSTITUTE OF ORIENTAL MEDICINE, Daejeon (KR)

(72) Inventors: Hwan Suck Chung, Daegu (KR); Ji Hye Kim, Daegu (KR); Jang Gi Choi, Daegu (KR); Eun-Ji Lee, Gyeongsangbuk-do (KR); Young Soo Kim, Gyeonggi-do (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 307 days.

(21) Appl. No.: 18/290,488

(22) PCT Filed: May 31, 2022

(86) PCT No.: PCT/KR2022/007716
§ 371 (c)(1),
(2) Date: Nov. 14, 2023

(87) PCT Pub. No.: WO2023/027301
PCT Pub. Date: Mar. 2, 2023

(65) Prior Publication Data

US 2024/0252577 A1 Aug. 1, 2024

(30) Foreign Application Priority Data

Aug. 27, 2021 (KR) ........................ 10-2021-0113855

(51) Int. Cl.

| | |
|---|---|
| ***A61K 36/73*** | (2006.01) |
| ***A61K 45/06*** | (2006.01) |
| ***A61P 35/00*** | (2006.01) |
| ***A61P 37/00*** | (2006.01) |

(52) U.S. Cl.
CPC .............. *A61K 36/73* (2013.01); *A61K 45/06* (2013.01); *A61P 35/00* (2018.01); *A61P 37/00* (2018.01); *A61K 2236/331* (2013.01); *A61K 2236/333* (2013.01)

(58) Field of Classification Search
CPC .. A61K 36/73; A61K 45/06; A61K 2236/331; A61K 2236/333; A61K 31/555; A61K 2300/00; A61P 35/00; A61P 37/00; A23L 19/00; A23L 33/105; A23V 2002/00; A23V 2200/308; A23V 2200/324; A23V 2250/21; A23V 2300/14
See application file for complete search history.

(56) References Cited

FOREIGN PATENT DOCUMENTS

| | | | |
|---|---|---|---|
| KR | 10-2005-0113290 | A | 12/2005 |
| KR | 10-2008-0008491 | A | 1/2008 |
| KR | 10-2012-0010733 | A | 2/2012 |
| KR | 10-2016-0102933 | A | 8/2016 |
| KR | 10-2020-0138121 | A | 12/2020 |
| KR | 10-2021-0057657 | A | 5/2021 |
| KR | 10-2290222 | B1 | 8/2021 |

OTHER PUBLICATIONS

Alcindor, T. and Beauger, N. Oxaliplatin: a review in the era of molecularly targeted therapy. Current Oncology 2011, 18 (1), 18-25. DOI: 10.3747/co.v18i1.708 (Year: 2011).*
Kim, J. H. et al. Unripe Black Raspberry (*Rubus coreanus* Miquel) Extract and Its Constitute, Ellagic Acid Induces T Cell Activation and Antitumor Immunity by Blocking PD-1/PD-L1 Interaction. Foods 2020, 9 (11), 1590. DOI: 10.3390/foods9111590 (Year: 2020).*
Office action issued on Apr. 24, 2024 from Korean Patent Office in a counterpart Korean Patent Application No. 10-2021-0113855 (all the cited references are listed in this IDS.) (English translation is also submitted herewith.).
Myoung Gun Choung et al., "Antioxidant, Anticancer and Immune Activation of Anthocyanin Fraction from *Rubus coreanus* Miquel fruits (Bokbunja)", Korean J. Medicinal Crop Sci., 20(4) : p. 259-269, 2012 (English Abstract is included in the first page.).
International Search Report for PCT/KR2022/007716 mailed on Aug. 26, 2022.

* cited by examiner

*Primary Examiner* — Anand U Desai
*Assistant Examiner* — Robert Franklin Spaine
(74) *Attorney, Agent, or Firm* — The PL Law Group, PLLC

(57) ABSTRACT

A composition for inhibiting proliferation of tumor comprising *Rubus coreanus* extract as effective component. It was found that the *Rubus coreanus* extract binds to PD-L1 present on the surface of cancer cells, thus blocking the interaction between cancer cells and PD-1 on the surface of T cells to activate T cells and exhibit an inhibitory effect on tumor proliferation, and it was also found that the *Rubus coreanus* extract shows an excellent anti-tumor immune activity in humanized PD-1 animal model induced with MC38 colorectal cancer expressing human PD-L1 and also a synergistic effect when co-administered with anti-cancer agents.

9 Claims, 3 Drawing Sheets

COMPOSITION FOR INHIBITING PROLIFERATION OF TUMOR COMPRISING *RUBUS COREANUS* EXTRACT AS EFFECTIVE COMPONENT

PRIORITY

This application claims benefit under 35 U.S.C. 119, 120, 121, or 365(c), and is a National Stage entry from International Application No. PCT/KR2022/007716, filed May 31, 2022, which claims priority to the benefit of Korean Patent Application No. 10-2021-0113855 filed in the Korean Intellectual Property Office on Aug. 27, 2021, the entire contents of which are incorporated herein by reference.

BACKGROUND

1. Technical Field

The present invention relates to a composition for inhibiting proliferation of tumor comprising *Rubus coreanus* extract as effective component.

2. Background Art

Conventional cancer treatments that are known to aim at conquering cancer typically involve surgery to remove tumor, along with the simultaneous use of radiation therapy and chemotherapy to reduce the tumor size before surgery or induce the death of remaining cancer cells and prevent recurrence after surgery. Radiation therapy and chemotherapy, which are referred to as the first-generation cancer therapies, include disrupting the process of uncontrolled infinite proliferation of cancer cells, leading to the induction of cancer cell death. However, radiation therapy poses a challenge as it induces not only DNA damage in cancer cells but also the death of normal cells through high-energy radiation, and chemotherapy for hindering the cell division process also has several problems as it does not specifically impede cancer cell division but also hinders the division of normal cells, leading to serious side effects such as decreased white blood cell count and hair loss.

To solve these problems, there has been an expectation that the development of targeted anti-cancer agents, known as the second-generation anti-cancer agents which selectively attack only cancer cells while sparing normal cells, would reduce the side effects associated with the first-generation anti-cancer agents. Meanwhile, targeted anti-cancer agents are characterized by selective inhibition of cancer cells by acting only on proteins that induce cancer. However, since the proteins inducing cancer and the proteins exhibiting therapeutic effects vary depending on the type of cancer, it is necessary to use anti-cancer agents that match the type of target protein.

Additionally, as cancer cells possess mechanisms to acquire resistance to targeted anti-cancer agents, they can develop 'immune evasion ability' by having mutations to prevent themselves from being targeted by immune cells, leading to situations where the targeted anti-cancer agent may fail to recognize cancer cells. Therefore, to reduce the side effects and resistance issues associated with anti-cancer treatments, development of third-generation immunotherapeutic agents for cancer is underway, which can solve those problems and allow immune cells to remember and continuously attack cancer cells even after treatment is discontinued.

Immunotherapy for cancer is a treatment approach that stimulates the body's immune system to boost its self-immunity, enabling immune cells to target and attack cancer cells. Immunotherapeutic anti-cancer agent focuses on enhancing the function of immune cells, awakening their 'potential to attack cancer cells.'

The immunotherapeutic anti-cancer agent can be categorized into immune checkpoint inhibitors, immune cell therapeutic agents, therapeutic antibodies, and anti-cancer vaccines. Immune checkpoint inhibitors are an anti-cancer agent for blocking the activity of immune checkpoint proteins that suppress T-cell function, thus activating T cells to attack cancer cells. Antibodies recognizing CTLA-4, PD-1, and PD-L1 are commonly used as an immune checkpoint inhibitor. Immune cell therapeutic agents are an anti-cancer agent for boosting cell-mediated immunity and they include natural killer (NK) cell therapeutic agents, T-cell therapeutic agents, and chimeric antigen receptor T-cell (CAR-T) therapeutic agents. As for the therapeutic antibodies, antibody-drug conjugates are used, where the antibody binds to cancer cells, and upon drug release, it attacks the cancer cells. Furthermore, anti-cancer vaccines involve administering to a cancer patient tumor-specific antigens present in cancer cells or protein/peptide molecules that can enhance overall immune responses within the patient, and they are an immunotherapy which aims to activate the immune system, making the internal immune functions more active to attack cancer cells.

Meanwhile, *Rubus coreanus*, known as bokbunja in Korea, belongs to the genus *Rubus* (raspberry). The genus *Rubus* is one of the most diverse plant genera, consisting of around 250 species with sexual reproduction, making it among the most diverse plant genera globally. It is composed of 12 subgenera, encompassing cultivated and wild species. Among them, one of the most valuable is *Rubus coreanus*. In traditional oriental medicine, the unripe fruit, i.e., immature fruit, of *Rubus coreanus* has been used and it is employed as a therapeutic agent for having healthy body or healthy eye, curing diarrhea, curing erectile dysfunction, or preventing hair loss, etc., and it is also used for a therapeutic agent for treating asthma and other allergy-related disorders.

The technology related to *Rubus coreanus* extract includes Korean Patent Application Publication No. 2016-0102933, which discloses a pharmaceutical composition with anti-angiogenic activity comprising water extract of *Rubus coreanus* as effective component. Additionally, Korean Patent Registration No. 2290222 discloses a composition for preventing or treating non-alcoholic fatty liver disease comprising *Rubus coreanus* extract as effective component. However, as of now, there is no disclosure of the composition of the present invention for inhibiting proliferation of tumor comprising *Rubus coreanus* extract as effective component.

SUMMARY

The present invention is devised under the aforementioned circumstances, and it provides a composition for inhibiting proliferation of tumor comprising *Rubus coreanus* extract as effective component. It is found that the *Rubus coreanus* extract binds to PD-L1 present on the surface of cancer cells, thus blocking the interaction between cancer cells and PD-1 on the surface of T cells to activate T cells and exhibit an inhibitory effect on tumor proliferation, and the *Rubus coreanus* extract shows an excellent anti-tumor immune activity in humanized PD-1 animal model induced with MC38 colorectal cancer expressing human PD-L1 and also a synergistic effect when co-administered with anti-cancer agents, and the present invention is completed accordingly.

To achieve the purpose described in the above, the present invention provides a functional health food composition for inhibiting immune checkpoint comprising *Rubus coreanus* extract as effective component.

The present invention further provides a pharmaceutical composition for preventing or treating a disorder relating to immune checkpoint inhibition comprising *Rubus coreanus* extract as effective component.

The present invention further provides an anti-tumor pharmaceutical composition comprising an anti-cancer active agent and *Rubus coreanus* extract as effective component.

The present invention still further provides an anti-cancer adjuvant comprising *Rubus coreanus* extract as effective component.

The present invention relates to a composition for inhibiting proliferation of tumor comprising *Rubus coreanus* extract as effective component. Specifically, the *Rubus coreanus* extract binds to PD-L1 present on the surface of cancer cells, thus blocking the interaction between cancer cells and PD-1 on the surface of T cells to activate T cells and exhibit an inhibitory effect on tumor proliferation, and it shows an excellent anti-tumor immune activity in humanized PD-1 animal model induced with MC38 colorectal cancer expressing human PD-L1 and also a synergistic effect when co-administered with anti-cancer agents.

BRIEF DESCRIPTION OF THE DRAWINGS

In FIG. 1A, the competitive enzyme-linked immunosorbent assay (Competitive ELISA) was used to assess the inhibitory activity of *Rubus coreanus* extract on PD-1/PD-L1 binding. FIG. 1B displays the result of determining the inhibitory activity of the positive control (αPD-1) on PD-1/PD-L1 binding using Competitive ELISA. FIGS. 1C and 1D show the result of determining cytotoxicity of *Rubus coreanus* extract in PD-1/NFAT Luciferase Reporter Jurkat T cells (constantly expressing PD-1 protein) and PD-L1/aAPC CHO-KI cells (constantly expressing immune checkpoint PD-L1 protein), respectively. FIG. 1E shows the result of determining, by using the NFAT luciferase reporter assay, the inhibitory activity of *Rubus coreanus* extract on PD-1/PD-L1 binding. FIG. 1F shows the result of determining the inhibitory activity of the positive control (αPD-1) on PD-1/PD-L1 binding using the NFAT luciferase reporter assay. The symbols *, , and * indicate a statistically significant decrease in inhibitory activity of *Rubus coreanus* extract or the positive control (αPD-1) on PD-1/PD-L1 binding compared to the untreated control, where * denotes $p<0.05$,  denotes $p<0.01$, and * denotes $p<0.001$. "ns" indicates no statistically significant change.

FIG. 2A shows the average mouse body weight following administration of the negative control (vehicle), positive control (αPD-1), or *Rubus coreanus* extract. FIG. 2B illustrates the change in tumor size following the administration of the negative control (vehicle), positive control (αPD-1), or *Rubus coreanus* extract. FIG. 2C displays photographs of the finally extracted tumors (scale size=1 cm), and FIG. 2D presents the average weight of the extracted tumors. The symbols *, , and * indicate a statistically significant decrease in tumor region or tumor weight in groups treated with *Rubus coreanus* extract or the positive control (αPD-1) compared to the untreated control, where * denotes $p<0.05$,  denotes $p<0.01$, and * denotes $p<0.001$ FIG. 3A Indicates the dosing period, frequency, and dosage of oxaliplatin and *Rubus coreanus* extract (RCE). FIGS. 3B to 3D represent graphs illustrating the changes in body weight (FIG. 3B), tumor volume (FIG. 3C), and tumor weight (FIG. 3D) following the administration of oxaliplatin and *Rubus coreanus* extract (RCE). FIG. 3E shows photographs of the tumors extracted and verified after the termination of the experiment. The symbol * signifies a statistically more significant decrease in tumor size and tumor weight in the group treated with both oxaliplatin and *Rubus coreanus* extract (RCE+Oxa) compared to the group treated with *Rubus coreanus* extract alone (RCE), with a significance of $p<0.05$.

DETAILED DESCRIPTION

Figure 1A:
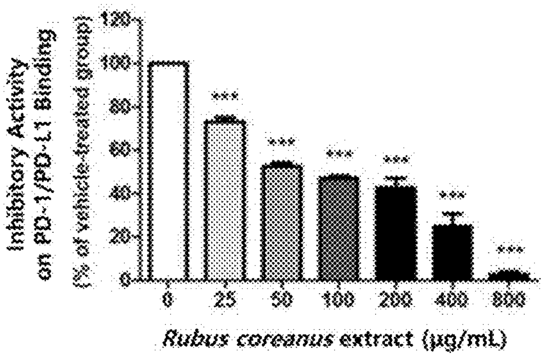
FIGS. 1A to 1F present the results of determining the immune checkpoint (PD-1/PD-L1) binding inhibitory effect of *Rubus coreanus* extract and the positive control (αPD-1).
Figure 1B:
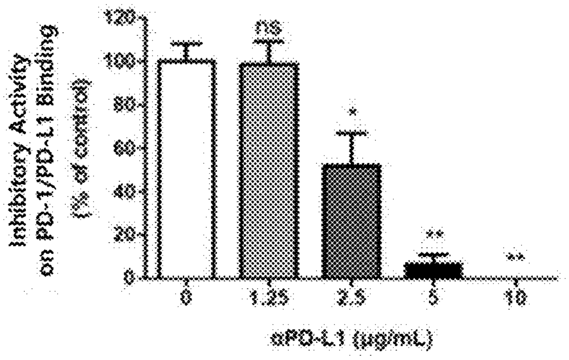
Figure 1C:
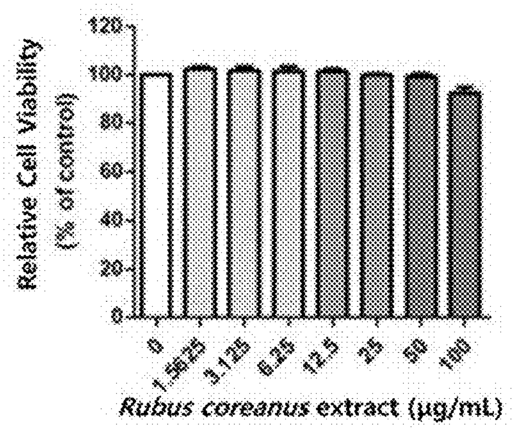
Figure 1D:
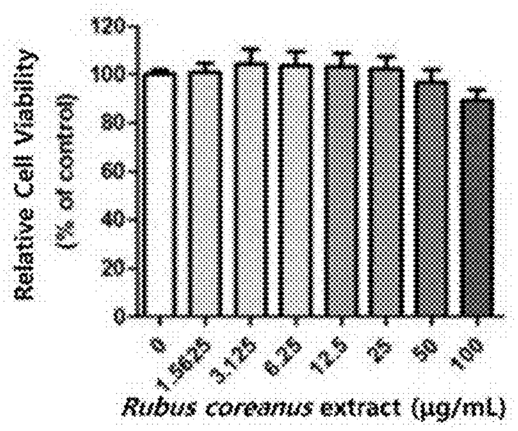
Figure 1E:
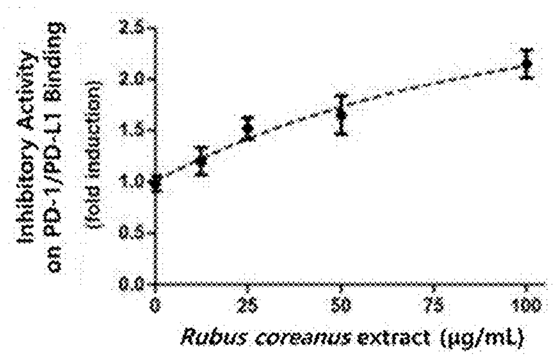
Figure 1F:
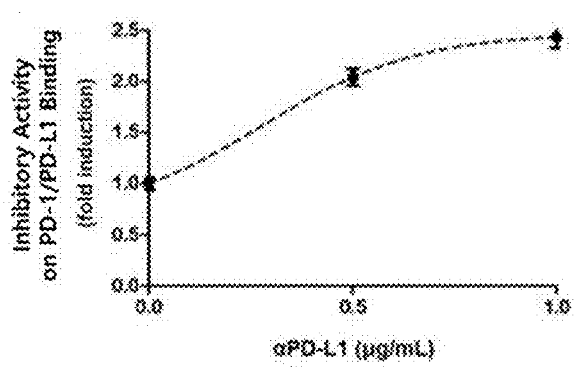

The present invention relates to a functional health food composition for inhibiting immune checkpoint comprising *Rubus coreanus* extract as effective component.

The *Rubus coreanus* extract can be produced by a method including the following steps:

(1) carrying out extraction by adding an extraction solvent to *Rubus coreanus;*

(2) filtering the extract of the step (1); and (3) concentrating under reduced pressure the extract filtered in the step (2) followed by drying to give extract, but the method is not limited thereto.

The extraction solvent of the above step (1) is preferably selected from water, $C_1$-$C_4$ lower alcohol, and a mixture thereof. It is more preferably water, and even more preferably hot water, but it is not limited thereto.

With regard to the production method described in the present invention, any kind of common methods that are generally known as extraction method in the pertinent art, e.g., filtration, hot water extraction, impregnation extraction, extraction by reflux condensation, and ultrasonic extraction, can be used. It is preferable that the extraction is carried out by adding the extraction solvent in an amount of 1 to 20 times the weight of dried *Rubus coreanus*. More preferably, the extraction solvent is added in an amount of 10 to 18 times the weight of dried *Rubus coreanus*. The extraction temperature is preferably between 90° C. and 110° C., but it is not limited thereto. Furthermore, the extraction time is preferably between 0.5 hour and 10 hours and more preferably between 0.5 hour and 5 hours, but it is not limited thereto. It is preferable that the concentration under reduced pressure of the step (3) in the above method is preferably carried out by using a vacuum concentration apparatus or a vacuum rotary evaporator, but it is not limited thereto. Additionally, the drying can be preferably performed by drying under reduced pressure, drying under vacuum, drying under boiling, spray drying, or freeze-drying, but it is not limited thereto.

The *Rubus coreanus* extract is characterized in that it targets PD-L1 or CD-80. The cancer cells may be preferably those derived from any one of liver cancer, lung cancer, breast cancer, melanoma, stomach cancer, colorectal cancer, rectal cancer, skin cancer, bladder cancer, prostate cancer, ovarian cancer, cervical cancer, thyroid cancer, kidney cancer, fibrosarcoma, and hematologic malignancy, but it is not limited thereto.

The functional health food composition of the present invention can be prepared by adding the *Rubus coreanus* extract by itself or mixing it with other food product or other food component. The composition can be suitably used by following a common method. Type of the functional health food composition is not particularly limited. Examples of the food product to which the *Rubus coreanus* extract of the present invention can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all functional health food products in general sense are included therein. The health beverage containing the composition of the present invention may include various flavorings or natural carbohydrates as additional ingredients, similar to regular beverages. The natural carbohydrates may include monosaccharides such as glucose and fructose, disaccharides such as maltose and sucrose, and polysaccharides such as dextrin and cyclodextrin, as well as sugar alcohols such as xylitol, sorbitol, and erythritol. As sweeteners, natural sweeteners such as thaumatin and *stevia* extracts, or synthetic sweeteners such as saccharin and aspartame, can be used. The ratio of the natural carbohydrates is generally about 0.01 to 0.04 g, preferably about 0.02 to 0.03 g per 100 g of the composition of the present invention.

The functional health food composition of the present invention may further comprise various nutritional supplements, a vitamin, an electrolyte, a flavor, a coloring agent, pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated beverage. Other than those, fruit juice or fruit pulp for producing vegetable beverage may be additionally comprised. Ratio of the additives is, although not critically important, preferably selected from a range of between 0.01 part by weight and 2 parts by weight relative to 100 parts by weight of the composition of the present invention.

The present invention further relates to a pharmaceutical composition for preventing or treating a disorder relating to immune checkpoint inhibition comprising *Rubus coreanus* extract as effective component.

The aforementioned disorder relating to immune checkpoint inhibition is preferably cancer, infection, sepsis, or immunosenescence, and more preferably cancer, but not limited thereto. The cancer is the same as those described above.

The present invention further relates to an anti-tumor pharmaceutical composition comprising an anti-cancer active agent and *Rubus coreanus* extract as effective component.

The aforementioned anti-cancer active agent is preferably an anti-cancer agent or an immune checkpoint inhibitor, but not limited thereto. Preferred examples of the anti-cancer agent include one or more selected from actinomycin D, bleomycin sulfate, daunomycin, daunorubicin, doxorubicin, epirubicin, idarubicin, mitomycin, mitomycin-C, mitramycin, irinotecan, camptothecin, novobiocin, epirubicin, dactinomycin, amsacrine, teniposide, etoposide, cisplatin, carboplatin, oxaliplatin, paclitaxel, docetaxel, gefitinib, erlotinib, and afatinib. Preferred examples of the immune checkpoint inhibitor include an anti-PD-L1 antibody, an anti-PD-1 antibody, an anti-CD-80 antibody, and an anti-CTLA-4 antibody, but are not limited thereto.

The pharmaceutical composition of the present invention can take various forms for oral or parenteral administration. When formulated, production is made by using commonly-used diluents or vehicles such as fillers, expanders, binders, wetting agents, disintegrants, or surfactants. For solid preparations intended for oral administration, they may include tablets, pills, powders, granules, capsules, etc., and these solid formulations are formulated by mixing one or more compounds with at least one vehicle such as starch, calcium carbonate, sucrose, lactose, gelatin, etc. Additionally, lubricants such as magnesium stearate, tale, etc. can be used in addition to simple vehicles. For liquid preparations intended for oral administration, they may include suspensions, solutions, emulsions, syrups, etc., and in addition to commonly used simple diluents like water and liquid paraffin, various vehicles such as wetting agents, sweeteners, flavors, preservatives, etc. may be included. For preparations intended for parenteral administration, they may include sterilized aqueous solutions, non-aqueous solvents, suspensions, emulsions, freeze-dried formulations, suppositories, etc. Examples of non-aqueous solvents and solvents for suspension include propylene glycol, polyethylene glycol, vegetable oils such as olive oil, injectable esters such as ethyl oleate, etc. Examples of suppository bases include WITEPSOL® (hydrogenated coconut glycerides, a hard fat suppository base), Macrogol, TWEEN® 61 (polysorbate, a nonionic surfactant), cocoa butter, laurin, glycerol gelatin, etc.

The pharmaceutical composition of the present invention can be administered either orally or parenterally, and when administered parenterally, it can be applied by topical application on skin, or an intraperitoneal, rectal, intravenous, intramuscular, subcutaneous, intrathecal, or intracerebrovascular injection method can be preferably selected.

The pharmaceutical composition according to the present invention is administered in a pharmacologically effective amount. In the present invention, the expression "pharmacologically effective amount" refers to an amount sufficient to treat a disease with a reasonable benefit/risk ratio applicable to medical therapy. The effective dosage level can be determined based on various factors, including the type and severity of the patient's condition, the activity of the drug, sensitivity to the drug, administration time, route of administration, elimination rate, treatment duration, factors including other drugs that are simultaneously used, and other well-known factors in the medical field. The pharmaceutical composition of the present invention can be administered as an individual therapeutic agent or in combination with other therapeutic agents, sequentially or simultaneously with conventional therapies, and in a single dose or multiple doses. It is important to administer, with consideration of the aforementioned factors, the minimum effective amount that can achieve maximum efficacy without having any adverse effects, and this can be readily determined by a person who is skilled in the pertinent art.

The dosage of the composition of the present invention may vary in range depending on the patient's weight, age, gender, health condition, diet, administration time, method of administration, elimination rate, and severity of the disease. The daily dosage ranges, based on the amount of *Rubus coreanus* extract, from 0.01 to 2,000 mg/kg. Preferably, it ranges from 30 to 500 mg/kg, and even more preferably from 50 to 300 mg/kg. The composition can be administered 1 to 6 times per day. The pharmaceutical composition of the present invention can be used either alone or in combination with surgery, radiation therapy, hormone therapy, chemotherapy, antibody therapy, and other treatment methods using biological response modifiers.

The present invention still further relates to an anti-cancer adjuvant comprising *Rubus coreanus* extract as effective component.

The anti-cancer adjuvant may comprise one or more additional active ingredients that exhibit the same or similar functions as *Rubus coreanus* extract. For clinical use, the anti-cancer adjuvant can be administered either orally or parenterally, and when administered parenterally, it can be applied by an intraperitoneal, rectal, subcutaneous, intravenous, intramuscular, intrathecal, intracerebrovascular, or thoracic injection method. The anti-cancer adjuvant may be used in form of common medicinal product.

The anti-cancer adjuvant can be used either alone or in combination with surgery, radiation therapy, hormone therapy, chemotherapy, and other treatment methods using biological response modifiers. The daily dosage of the anti-cancer adjuvant is about from 0.0001 to 100 mg/kg. Preferably, it ranges from 0.001 to 10 mg/kg, and it can be preferably administered once a day or divided into several doses, but may vary in range depending on the patient's weight, age, gender, health condition, diet, administration time, method of administration, elimination rate, and severity of the disease. The anti-cancer adjuvant of the present invention can be, when formulated for actual clinical administration, administered in various parenteral dosage forms. In the case of formulation, it is usually formulated using diluents or vehicles such as fillers, expanders, binders, wetting agents, disintegrants, surfactants, or the like. For preparations intended parenteral administration, sterilized aqueous solutions, non-aqueous solvents, suspensions, emulsions, freeze-dried formulations, suppositories, etc. are included. Examples of non-aqueous solvents and solvents for suspension include propylene glycol, polyethylene glycol, vegetable oils such as olive oil, injectable esters such as ethyl oleate, etc. Examples of suppository bases include WITEPSOL® (hydrogenated coconut glycerides, a hard fat suppository base), Macrogol, TWEEN® 61 (polysorbate, a nonionic surfactant), cocoa butter, laurin, glycerol gelatin, etc.

Hereinbelow, the present invention is explained in greater detail in view of Examples. However, the following Examples are given only for more specific explanation of the present invention and it is evident to a person who has common knowledge in the pertinent art that the scope of the present invention is not limited by them.

EXAMPLES

Example 1. Preparation of *Rubus coreanus* Extract

Fifty kilograms of dried *Rubus coreanus* were dried and then added with 800 L of purified water as a solvent, and subjected to hot water extraction at 100° C. over 3 hours. The resulting extract was concentrated under reduced pressure to obtain *Rubus coreanus* extract.

Example 2. Determination of Inhibitory Activity of *Rubus coreanus* Extract on Binding of Immune Checkpoint PD-1 and PD-L1

Using competitive ELISA analysis, it was found that the *Rubus coreanus* ethanol extract competitively binds to PD-L1 in a concentration-dependent manner, thus blocking the interaction with PD-1.

The competitive ELISA analysis was performed using a PD-1/PD-L1 inhibitor ELISA screening kit by following the manufacturer's instructions. The procedure involves coating a 96-well plate with recombinant human PD-L1 (1 pg/mL dissolved in PBS, 100 pL/well) overnight. The plate was then washed with PBS (PBS-T) containing 0.1% TWEEN® (polysorbate, a nonionic surfactant) and blocked with 2% (w/v) BSA in PBS for 1 hour at room temperature. After another round of washing, biotinylated hPD-1 (0.5 pg/mL, 50 pL/well) was added to each well, and the plate was incubated for 2 hours at room temperature. Following three washes with PBS-T, streptavidin conjugated with HRP (0.2 pg/mL, 50 pL/well) was added to each well, and the plate was incubated for 1 hour. Following the incubation, after a final wash with 0.1% PBS-T three times, relative chemiluminescence was measured using a SPECTRAMAX® L luminometer.

The results indicate that the binding of PD-1/PD-L1 is inhibited in concentration dependent manner. Furthermore, the *Rubus coreanus* extract reduced in a concentration dependent manner the binding of PD-1/PD-L1, with statistical significance. As a result of determining cytotoxicity of *Rubus coreanus* extract in PD-1/NFAT Luciferase Reporter Jurkat T cells which constantly express immune checkpoint PD-1 protein under normal conditions, it was found that the cytotoxicity of *Rubus coreanus* extract is minimal (FIGS. 1A to 1F).

Additionally, it was also found with an intracellular experiment that co-cultivation of PD-1/NFAT Luciferase Reporter Jurkat T cells, which constantly express immune checkpoint PD-1 and PD-L1, and PD-L1/aAPC CHO-KI cells followed by a treatment with *Rubus coreanus* extract resulted in an enhancement of T cell activity, reaching up to twice the baseline, through immune checkpoint blockade (FIGS. 1A to 1F).

Example 3. Determination of Immunity and Effect of Inhibiting Tumor Proliferation as a Result of Administering *Rubus coreanus* Extract Male hPD-1 C57BL/6J mice were induced with tumors by subcutaneously injecting MC38 mouse colorectal cancer cells expressing hPD-L1. Using mice with pancreatic cancer tumors, the anti-tumor immunity shown after oral administration of immune checkpoint-blocking *Rubus coreanus* extract was investigated. The *Rubus coreanus* extract was orally administered at dose of 50 or 100 mg/kg, with six mice assigned to each test group, and the treatment lasted for approximately 3 weeks.

(1) During the test period, general symptoms were observed, and measurements were taken for body weight and food intake. After the completion of the administration and observation period, post-mortem examinations were carried out.

Figure 2A:
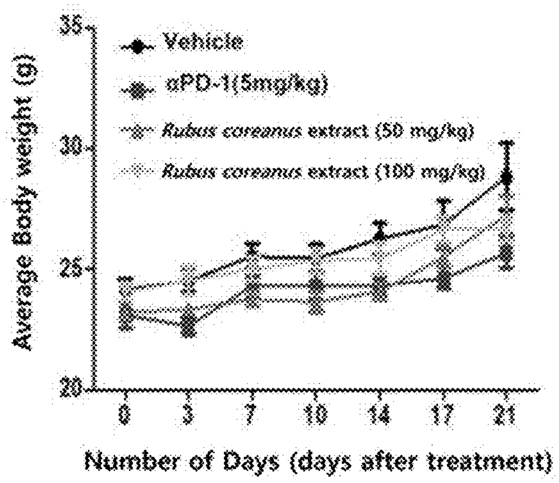
FIGS. 2A to 2D depict the results regarding the anti-tumor immune efficacy of *Rubus coreanus* extract in a Humanized PD-1 animal model induced with MC38 colorectal cancer expressing Human PD-L1.

The results showed that no significant increase or decrease in mouse body weight was caused by the administration of test substance during the test period. This suggests that the oral administration of the test substance did not lead to a notable toxicity in mice (FIG. 2A).

Figure 2B:
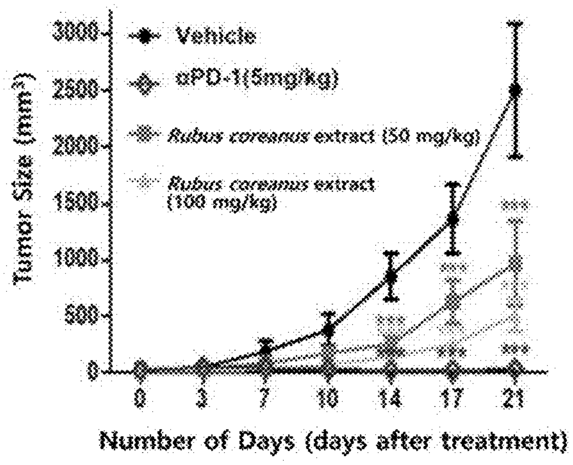
Figure 2C:
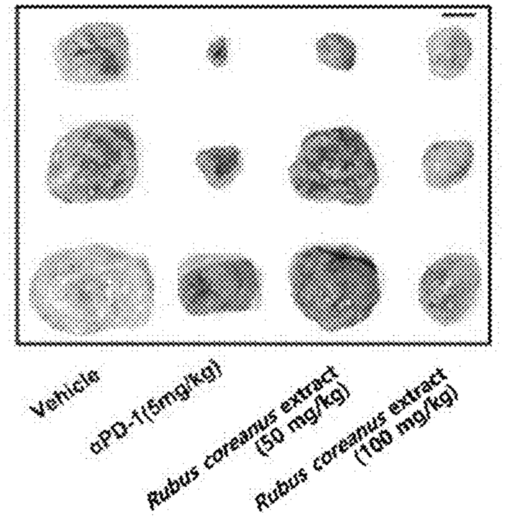
Figure 2D:
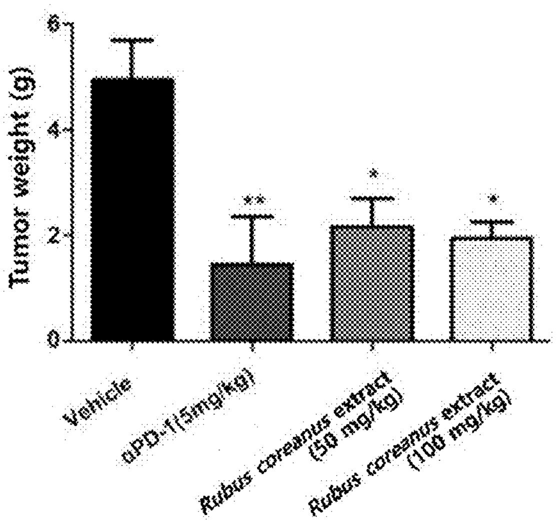
Figure 3A:
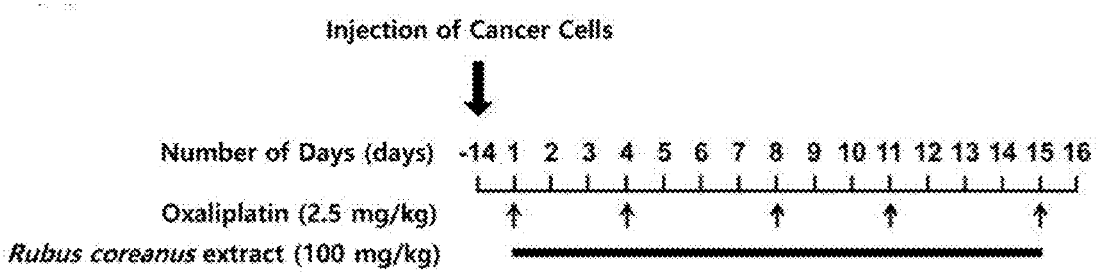
FIGS. 3A to 3E present the results of the animal test involving the combined administration of *Rubus coreanus* extract and oxaliplatin, which is an anti-cancer agent for treating colorectal cancer.
Figure 3B:
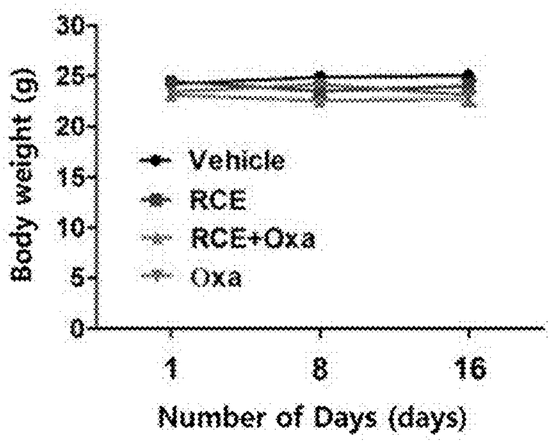
Figure 3C:
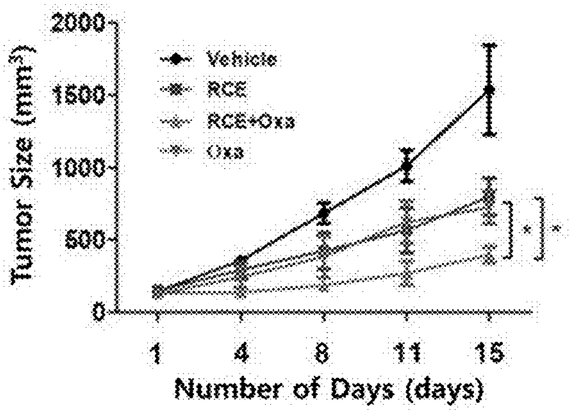
Figure 3D:
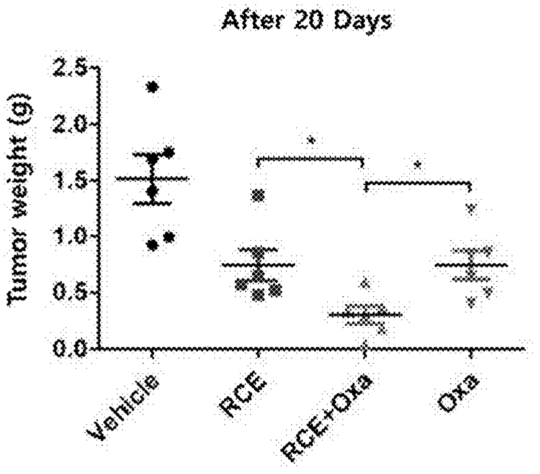
Figure 3E:
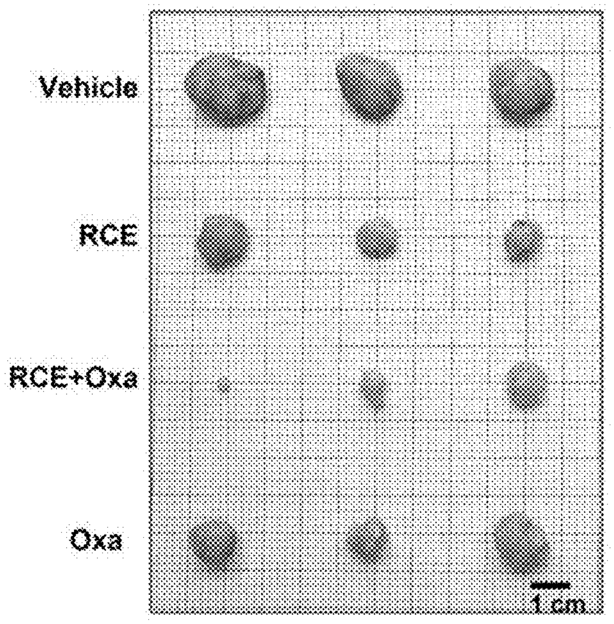

(2) When comparing the degree of tumor proliferation with the control, it was observed that in all test groups, there was a common decrease in tumor size due to the administration *Rubus coreanus* extract at dose of 50 or 100 mg/kg. In the positive control treated with PD-1 blocking antibody at a dose of 5 mg/kg, the tumors that were initially formed either completely disappeared or showed a significant decrease in proliferation (FIGS. 2B to 2D).

Example 4. Determination of Effect of Co-Administration of *Rubus coreanus* Extract and Oxaliplatin Male C57BL/6J mice, in which mouse PD-1 (mPD-1) was removed and replaced with human PD-1 (hPD-1), were induced with pancreatic cancer tumors by subcutaneously injecting MC-38 mouse colorectal cancer cells in which mouse PD-L1 (mPD-L1) was removed and replaced with human PD-L1 (hPD-L1). Six mice were used in each test group. As described in FIGS. 3A to 3E, the mice were treated with intervals using *Rubus coreanus* extract (100 mg/kg) or oxaliplatin (2.5 mg/kg), or a combination of both, i.e., *Rubus coreanus* extract (100 mg/kg) and oxaliplatin (2.5 mg/kg). Thereafter, the body weight and tumor size were measured at different time point.

The results showed that there was no significant difference in body weight among the test groups over time. However, compared to the group induced with colorectal cancer (vehicle), both the group receiving *Rubus coreanus* extract alone and the co-administration group of *Rubus coreanus* extract and oxaliplatin exhibited a significant decrease in tumor size and tumor weight.

Furthermore, the co-administration group of *Rubus coreanus* extract and oxaliplatin showed a more significant decrease in tumor size and tumor weight compared to the group receiving *Rubus coreanus* extract alone (FIGS. 3A to 3E).

What is claimed is:

1. A method for inhibiting an immune checkpoint, the method comprising administering to a subject in need thereof a composition comprising a *Rubus coreanus* extract as an effective component, wherein the immune checkpoint inhibition is between PD1 and PD-L1 on a cancer cell.

2. The method of claim 1, wherein the *Rubus coreanus* extract is prepared by using an extraction solvent selected from the group consisting of water, $C_1$-$C_4$ lower alcohol, and a mixture thereof.

3. The method of claim 1, wherein the cancer cell is derived from any one of liver cancer, lung cancer, breast cancer, melanoma, stomach cancer, colorectal cancer, rectal cancer, skin cancer, bladder cancer, prostate cancer, ovarian cancer, cervical cancer, thyroid cancer, kidney cancer, fibrosarcoma, and hematologic malignancy.

4. A method for treating a cancer relating to an immune checkpoint inhibition, the method comprising administering to a subject in need thereof a composition comprising a *Rubus coreanus* extract as an effective component, wherein the immune checkpoint inhibition is between PD1 and PD-L1 on a cancer cell.

5. The method of claim 4, wherein the cancer is selected from the group consisting of liver cancer, lung cancer, breast cancer, melanoma, stomach cancer, colorectal cancer, rectal cancer, skin cancer, bladder cancer, prostate cancer, ovarian cancer, cervical cancer, thyroid cancer, kidney cancer, fibrosarcoma, and hematologic malignancy.

6. The method of claim 4, wherein the composition further comprises an anti-cancer active agent.

7. The method of claim 6, wherein the anti-cancer active agent is an anti-cancer agent or an immune checkpoint inhibitor.

8. The method of claim 6, wherein the anti-cancer active agent is an anti-cancer agent selected from the group consisting of actinomycin D, bleomycin sulfate, daunomycin, daunorubicin, doxorubicin, epirubicin, idarubicin, mitomycin, mitomycin-C, mitramycin, irinotecan, camptothecin, novobiocin, epirubicin, dactinomycin, amsacrine, teniposide, etoposide, cisplatin, carboplatin, oxaliplatin, paclitaxel, docetaxel, gefitinib, erlotinib, afatinib, and a combination thereof.

9. The method of claim 6, wherein the anti-cancer active agent is an immune checkpoint inhibitor selected from the group consisting of an anti-PD-L1 antibody, an anti-PD-1 antibody, an anti-CD-80 antibody, an anti-CTLA-4 antibody, and a combination thereof.

* * * * *